United States Patent [19]

Stevens

[11] Patent Number: 4,936,845

[45] Date of Patent: Jun. 26, 1990

[54] CATHETER SYSTEM HAVING DISTAL TIP FOR OPENING OBSTRUCTIONS

[75] Inventor: Robert C. Stevens, Williston, Fla.

[73] Assignee: Cordis Corporation, Miami, Fla.

[21] Appl. No.: 370,115

[22] Filed: Jun. 21, 1989

Related U.S. Application Data

[63] Continuation of Ser. No. 83,859, Aug. 10, 1987, abandoned, which is a continuation-in-part of Ser. No. 27,186, Mar. 17, 1987, abandoned.

[51] Int. Cl.$^5$ ............................................. A61B 17/00
[52] U.S. Cl. ..................................... 606/159; 606/171; 606/180; 604/22
[58] Field of Search ............. 604/22; 128/303 R, 304, 128/305, 305.1, 751–755; 606/159, 170, 171, 180

[56] References Cited

U.S. PATENT DOCUMENTS

| | | |
|---|---|---|
| 3,525,339 | 8/1970 | Halligan . |
| 3,614,953 | 10/1971 | Moss et al. . |
| 3,732,858 | 5/1973 | Banko ................................. 604/22 |
| 3,749,085 | 7/1973 | Willson et al. .................... 128/305 |
| 3,811,446 | 5/1974 | Lerwick et al. . |
| 3,976,077 | 8/1976 | Kerfoot, Jr. ....................... 128/305 |
| 4,111,208 | 9/1978 | Leuenberger .................... 128/305.1 |
| 4,445,509 | 5/1984 | Auth . |
| 4,589,412 | 5/1986 | Kensey . |
| 4,646,736 | 3/1987 | Auth ................................. 128/303 R |
| 4,681,106 | 7/1987 | Kensey et al. ..................... 604/22 |
| 4,686,982 | 8/1987 | Nash .................................. 128/305 |
| 4,728,319 | 3/1988 | Masch ............................... 604/22 |
| 4,747,406 | 5/1988 | Nash .................................. 604/22 |
| 4,747,821 | 5/1988 | Kensey et al. ..................... 604/22 |
| 4,749,376 | 6/1988 | Kensey et al. ..................... 604/22 |
| 4,784,636 | 11/1988 | Rydell ............................... 604/22 |
| 4,795,438 | 1/1989 | Kensey et al. ..................... 604/22 |
| 4,798,586 | 1/1989 | Stevens ............................. 604/22 |
| 4,854,325 | 8/1989 | Stevens ............................. 604/164 |

FOREIGN PATENT DOCUMENTS

| | | | |
|---|---|---|---|
| 167927 | 1/1986 | European Pat. Off. ............ 128/305 |
| 442795 | 9/1974 | U.S.S.R. ............................. 128/305 |
| 1235321 | 6/1971 | United Kingdom . |
| 2093353 | 9/1982 | United Kingdom ................ 128/305 |

OTHER PUBLICATIONS

*Cardiovascular News*, McMahon Publishing Co., "High RPM Rotary Blade for Angioplasty Tested", 2/1986, pp. 1, 4.

Primary Examiner—Stephen C. Pellegrino
Assistant Examiner—Ralph Lewis
Attorney, Agent, or Firm—Watts, Hoffmann, Fisher & Heinke

[57] ABSTRACT

A drive catheter having a distal tip for opening a partially or totally obstructed blood vessel. Both manual and motor applied motions are disclosed. In addition to a continuous rotation, two reciprocating motions are disclosed. One reciprocating motion is a back and forth translation of the tip in a ramming motion. A second reciprocating motion is a back and forth rotation about an axis. Different shaped tips are disclosed for the two reciprocating motions.

2 Claims, 12 Drawing Sheets

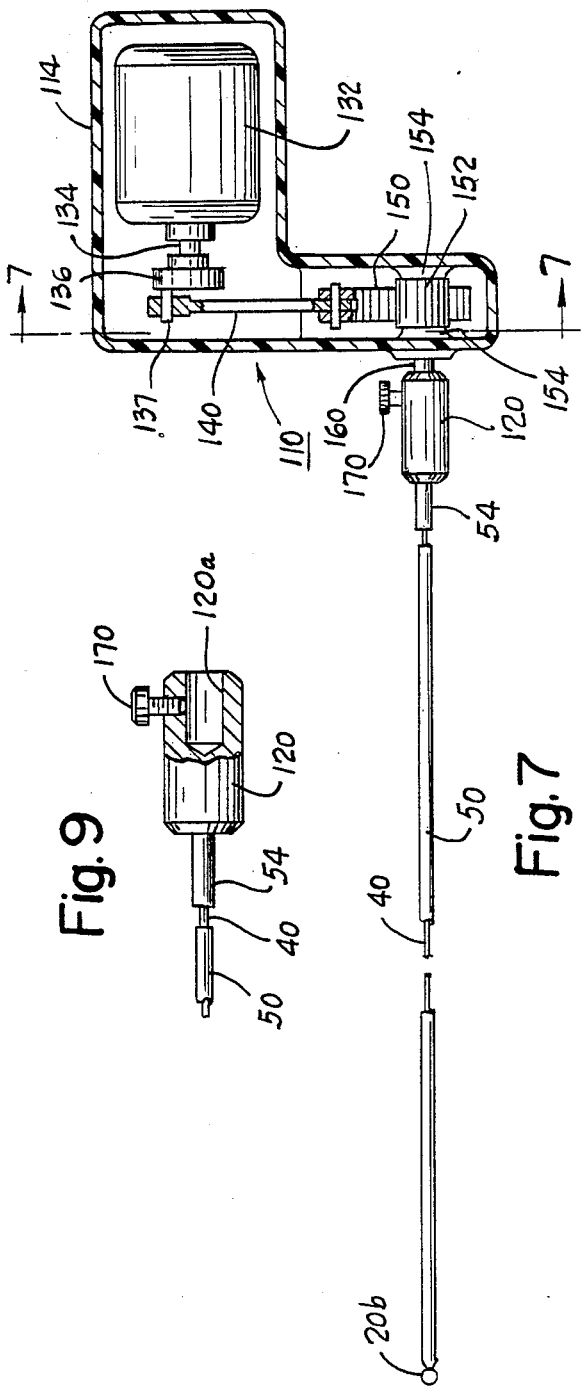
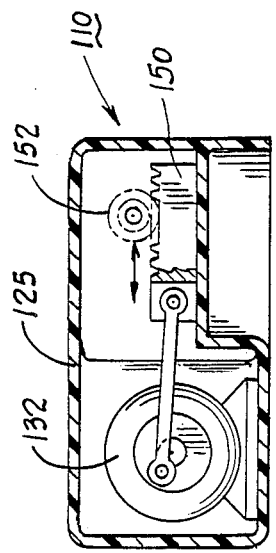
Fig. 9
Fig. 7
Fig. 8 ptent 4,936,845

CATHETER SYSTEM HAVING DISTAL TIP FOR OPENING OBSTRUCTIONS

RELATED APPLICATION

This is a continuation of co-pending application Ser. No. 07/083,859 filed on Aug. 10, 1987, now abandoned which is a continuation-in-part of U.S. patent application entitled "Catheter System Having a Small Diameter Rotatable Drive Member" filed Mar. 17, 1987, Ser. No. 07/027,186, now abandoned.

TECHNICAL FIELD

The present invention relates to a catheter system for opening a totally or partially occluded blood vessel.

BACKGROUND ART

Arteriosclerosis causes a partial or, in extreme cases, a total blockage of a blood vessel due to a build up of deposits along an inner surface of the blood vessel. The increase in the number of coronary by-pass operations is some indication of the incidence with which the problem is encountered in older patients.

Prior art proposals recognize that one alternative to bypassing a partially or totally blocked region in a blood vessel is to open or widen the blocked blood vessel. One prior art technique for reopening a blocked blood vessel is to insert a balloon catheter inside the vessel to expand the vessel and either break loose deposits within the vessel or alternatively, increase the size of the lumen passing through those deposits.

An alternate proposal for opening a blocked blood vessel is to bring a high-speed rotating device into contact with occluded portions of the blood vessel. The rotating device produces cutting, abrading, or fluid turbulence to open the vessel and increase blood flow. One device intended for physically opening the blood vessel in this manner is disclosed in U.S. Pat. Ser. No. 3,614,953 to Moss entitled "Improvements In or Relating To Drills for Clearing Obstructions". In this patent, a high-speed motor rotates a flexible drive shaft connected to a cutting bit. The bit and flexible drive shaft are inserted into an occluded blood vessel so that when the bit is rotated at high speed and moved into contact with occluded regions it breaks loose deposits within the blood vessel.

A more recent prior art patent disclosing a similar system for opening a blocked blood vessel is disclosed in U.S. Pat. Ser. No. 4,445,509 to Auth entitled "Method and Apparatus for Removal of Enclosed Abnormal Deposits". This patent describes a differential cutting tool mounted at a distal end of a flexible shaft which can be inserted into an occluded blood vessel. Again, high speed rotation of the cutting tool causes the tool to remove abnormal deposits from inside the blood vessel.

U.S. Pat. Ser. No. 4,589,412 to Kensey entitled "Method and Apparatus for Surgically Removing Remote Deposits" discloses a procedure for removing atherosclerotic plaque. A cutting tip is rotated by the application of fluid pressure through a multi-lumen catheter.

The proposals in the above-mentioned U.S. patents use high speed rotation of a distally located catheter tip to open a passageway through a blood vessel obstruction. Bringing a tip rotating at high speed into contact with blood vessel obstructions requires careful physician manipulation of the catheter. If the distal tip contacts the blood vessel wall with sufficient force the wall can be damaged or even punctured.

DISCLOSURE OF THE INVENTION

In accordance with one aspect of the present invention a reciprocating motion is applied to the distal tip portion of a drive catheter to open a partially or totally blocked blood vessel. This reciprocating, or back and forth movement appears to have merit at both low and at high speed.

In accordance with an additional aspect of the present invention a drive catheter is inserted into an elongated guide catheter and manually rotated or reciprocated at low speed to open an obstructed region of a blood vessel. The physician conducting the procedure monitors progress of both the drive catheter and guide catheter on a imaging screen. The guide catheter is advanced toward the obstructed region of the blood vessel in a co-ordinated fashion with the drive catheter.

A catheter system constructed in accordance with the invention includes an elongated flexible drive having a distal tip portion for opening an obstructed region of a blood vessel by physically opening a passageway through the obstructed region. An elongated flexible drive has a length sufficient to extend from outside the patient to the obstructed region within the blood vessel. A proximal end of the drive catheter outside the patient is used to impart motion to the distal tip via the flexible drive. In accordance with one procedure a rotation and/or a reciprocating motion is manually applied by the physician. The physician grasps the proximal end of the drive catheter and rotates the proximal end in either a continuous or back and forth manner to bore through the obstructed region.

A drive motor can be used to supplement or replace the manual motion imparted by the physician. The motor can impart a continuous rotation or a reciprocating motion to the flexible drive and thus the distal tip.

The reciprocating motion option can be a rotating motion, an in and out translating motion, or a combination of rotation and translation. Even when reciprocating at high speed, the reciprocating action results in controlled contact with the obstruction since the amount of rotation and/or translation is limited. Use of the invention also makes it less likely that material lining the blood vessel inner wall will be dislodged from the blood vessel and wrap around the distal tip in an uncontrolled manner.

One object of the invention is a new and improved drive catheter method and system for opening a passageway through an obstructed blood vessel. This and other objects, advantages and features of the invention will become better understood from a detailed description of a preferred embodiment of the invention which is described in conjunction with the accompanying drawings.

BRIEF DESCRIPTION OF THE DRAWINGS

FIG. 7 is a partially sectioned elevation view of an alternate drive system for imparting a reciprocating rotating motion to the distal end of the drive catheter;

FIG. 8 is a view of the alternate drive system as seen from the plane defined by the line 8—8 in FIG. 7;

FIG. 9 is an enlarged elevation view of a connector for coupling the FIG. 7 drive catheter to the drive system;

BEST MODE FOR CARRYING OUT THE INVENTION

Figure 1:
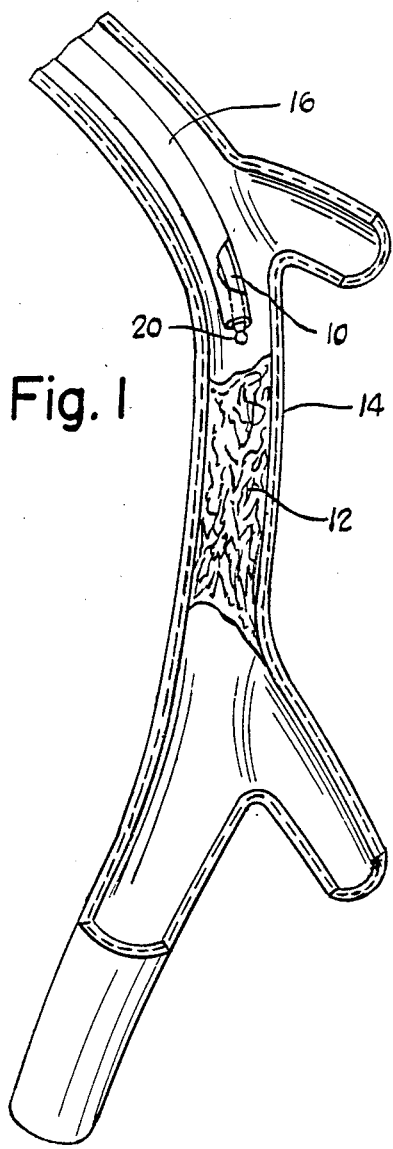
FIG. 1 schematically depicts a distal end of a drive catheter positioned within a guide catheter and approaching a region of total occlusion within a blood vessel.

Turning now to the drawings, FIG. 1 schematically illustrates a drive catheter 10 as the drive catheter 10 approaches an obstruction 12 in a blood vessel 14. The drive catheter 10 is inserted into a guide catheter 16 which has been previously inserted by a physician with the aid of an angiographic imaging system (not shown). The guide catheter 16 is conventional and has been utilized in the prior art for positioning balloon catheters within a patient. The imaging system enables the physician to monitor movement of both the guide catheter 16 and drive catheter 10. The obstruction 12 may include calcified (hard) or fatty (soft) deposits that have built up around the blood vessel inner wall. In extreme instances, the blood vessel may be completely blocked so that blood flow through the vessel is entirely cut off. The situation depicted in FIG. 1 is one in which the deposits have built up to completely cut off blood flow through the blood vessel 14.

Figure 2:
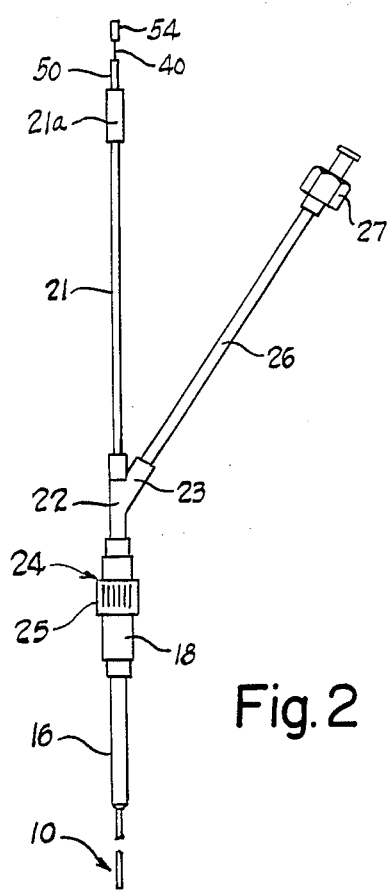
FIG. 2 is an elevation view of a proximal end of the FIG. 1 drive catheters.

While positioning the guide catheter 16, radio-opaque dye is injected through a leur hub 18 (FIG. 2) at the proximal end of the drive catheter 16 through a syringe or the like. To insert the drive catheter 10 the physician disconnects the syringe from the leur hub 18, removes the drive catheter 10 from a sterilized package, and inserts a distal tip 20 (FIG. 1) of the drive catheter 10 into the guide catheter 16. Before it is packaged the catheter 10 is inserted through a tube 21 coupled to a plastic bifurcated "Y" connector 22 having a side-arm branch 23 for injection of fluids. At one end the tube includes a collar 21a having an opening for receipt of the drive catheter 10. A conventional rotating adapter 24 coupled to the "Y" connector 22 has a leur fitting 25 that engages the leur hub 18 of the guide catheter 16. This allows the "Y" connector 22 to rotate while allowing saline/dye solutions to be injected from the side branch.

Coupled to the side-arm branch 23 is a flexible tube 26 and a conventional leur fitting 27 for injecting fluid into the catheter 16. The leur fitting is used for injecting controlled concentrations of opaque dye and saline solution as the blocked region of the vessel is opened. A seal (not shown) inside the "Y" connector 22 prevents the saline/dye solution that is pumped into the catheter 16 via the side-arm 23 from leaking from the connector 22 into the tube 21.

Figure 3:
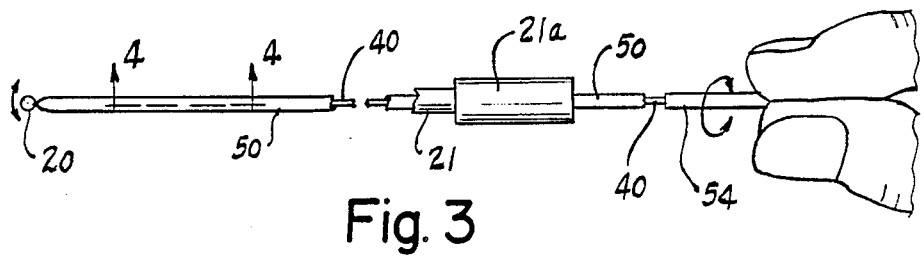
FIG. 3 is an enlarged elevation view illustrating both the proximal and distal portions of a drive catheter as the drive catheter is manually rotated by a physician.
Figure 4:
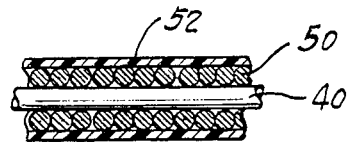
FIG. 4 is a section view as seen from the plane defined by the line 4—4 in FIG. 3.

The drive catheter 10 (FIGS. 3 and 4) includes a drive wire 40 rotatably mounted within a sleeve bearing 50 that passes through the in-line branch of the "Y" connector 22 into the guide catheter 16. The sleeve bearing 50 comprises a tightly coiled wire wound on a mandrel and may preferably be coated with a thin teflon coating for lubricity. Once the wire has been wound about the mandrel and coated, it is separated from the mandrel and defines a flexible tube or sheath having a center passageway suitable for receipt of the drive wire 40. The drive wire is inserted through the bearing 50 and the distal tip 20 and a cylindrical drive bushing 54 attached (by welding or the like) to opposite ends of the drive wire.

MANUAL PROCEDURE

To open a passageway through the blood vessel obstructions 12 the physician positions a distal end of the guide catheter 16 at one end of the obstruction 12 inserts the drive catheter 10 and pushes the distal tip 20 of the drive catheter 10 beyond the guide catheter 16 into contact with the obstruction.

The distal tip portion 20 of the drive catheter 10 is then manually rotated (FIG. 3) in either a continuous or reciprocating back and forth manner. As the distal tip 20 contacts the obstruction 12 a combined abrasion and cutting action takes place as the physician pushes the tip 20 into and through the obstruction 12. During this manual manipulation the physician grasps the drive bushing 54 and rotates the drive wire 40 within the bearing. The physician monitors this procedure on a viewing screen (contrast dye can be injected through the side arm 23 if necessary) and co-ordinates insertion of both the guide catheter 16 and the drive catheter 10 so that the distal tip 20 never extends too far beyond the distal end of the guide catheter 16.

Different procedures can be conducted using the drive catheter of the invention. In one procedure, a first drive catheter 10 having a distal tip is utilized to form a first passageway and succeedingly larger drive catheters also having other tips are routed to the vicinity of the obstruction 12 by simply removing one drive catheter and inserting a next larger size drive catheter into the guide catheter 16. In an alternate procedure, the drive catheter 20 is used to form an initial through-passage in the obstruction 12 and a balloon catheter (not shown) is substituted for the drive catheter 10 and inserted to a position spanning the obstruction 12. A balloon is then inflated to break loose or compress the obstructions clinging to the inner wall of the blood vessel.

MOTORIZED PROCEDURE

In addition to manual manipulation of the drive catheter 10, the present invention envisions use of a motor to apply rotation or reciprocating motion to the tip 20. Parent application Ser. No. 07/027,186 discloses the use of a hand-held motor which when energized with a battery produces rotational motion of a distal tip. When coupled to the drive bushing by a suitable adapter 120 (FIG. 9) an output shaft of a motor can be used to replace or supplement the manual manipulation. In addition two reciprocating or back and forth motions are disclosed that can be used in conjunction with or as replacements for the manual manipulation of the drive catheter 10.

Figure 11:
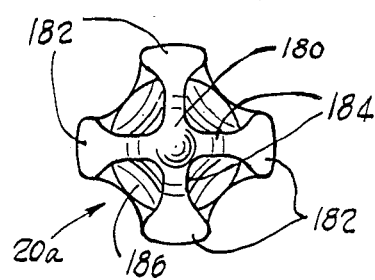
FIGS. 11 and 12 are end and side views of an alternate distal tip configuration for use with the FIG. 1 drive catheter.
Figure 12:
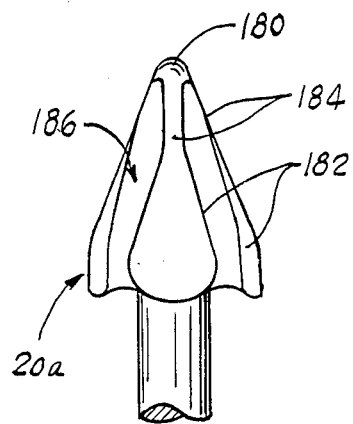

One reciprocating motion which is applied to the distal tip 20 is an in and out translation which causes a distal tip 20a shown in more detail in FIGS. 11 and 12 to contact the obstructions 12 with a ramming motion on each outward excursion.

Figure 5:
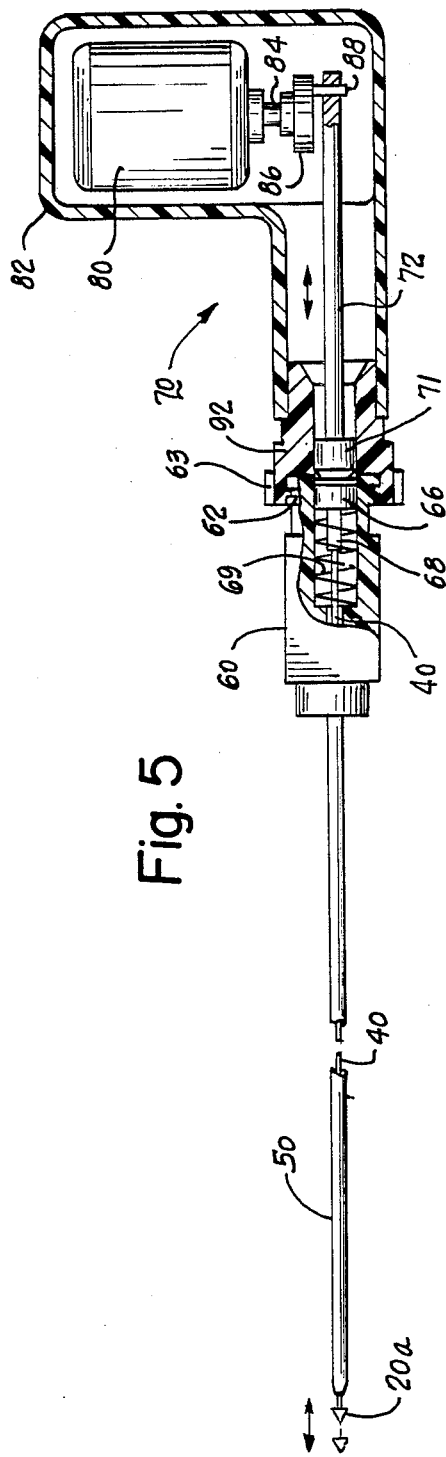
FIG. 5 is a partially sectioned elevation view of a drive system for imparting a reciprocating in and out motion to a drive catheter distal tip.
Figure 6:
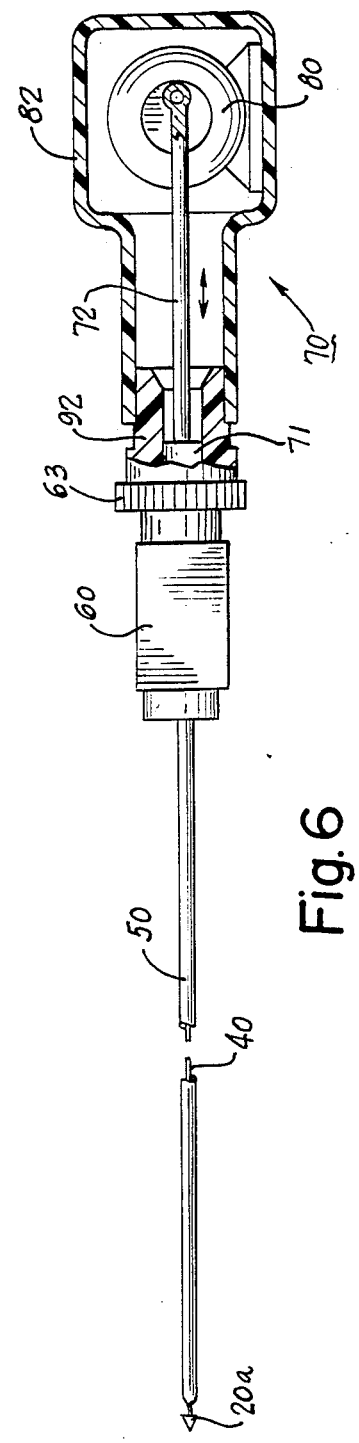
FIG. 6 is a partially sectioned plan view of the FIG. 5 drive system.

FIGS. 5 and 6 show a drive catheter 10 having a proximal coupling 60 (instead of the drive bushing 54) for transmitting a reciprocating in and out motion to the drive wire 40 (FIG. 5) and reciprocating distal tip 20a. The coupling 60 includes a leur fitting attached to a proximal end of the bearing 50. The leur fitting defines a threaded flange 62 which engages a connector 63 of a hand-held physician controlled catheter drive unit 70.

A cavity 64 within the leur fitting 60 supports a cylindrical drive 66 attached to the drive wire 40 by a coupling 68. A compressed spring 69 trapped between the cylindrical drive 66 and an end surface of the cavity 64 stores energy during an movement of the drive 66 into the cavity 64 and releases that energy on each return stroke.

When the leur fitting is coupled to the connector 63 the drive 66 engages a plunger 71 connected to the end of a reciprocating drive shaft 72. On each inward excursion of the drive 66 the drive wire 54 is pushed through the bearing 50 causing the tip 20a to drive out away from the bearing 50 and on the return stroke the tip 20a is retracted back toward the bearing 50.

The reciprocating drive shaft 72 is driven by a motor 80 mounted within the drive unit 70. The drive unit 70 includes a plastic housing 82 and motor support 83 to fix the motor 80. A motor actuator (not shown) allows a physician to controllably activate the motor 80 and in one embodiment, includes a slide actuator to allow motor speed to be continuously varied over an operating range. The preferred motor 80 is a d.c. battery powered motor for producing a rotation resulting in approximately 1500 back and forth cycles per minute.

A motor output shaft 84 (FIG. 5) is coupled to an eccentric wheel 86 having an outwardly extending pin 88 connected to the reciprocating drive shaft 72. The plunger 71 connected to the drive shaft 72 moves with a back and forth motion in a bearing 92 defined in the housing 82. As is apparent to one familiar with the eccentric drive illustrated in FIGS. 5 and 6, rotational motion of the motor output shaft 84 is converted to translational in and out motion of the plunger 71.

Figure 10:
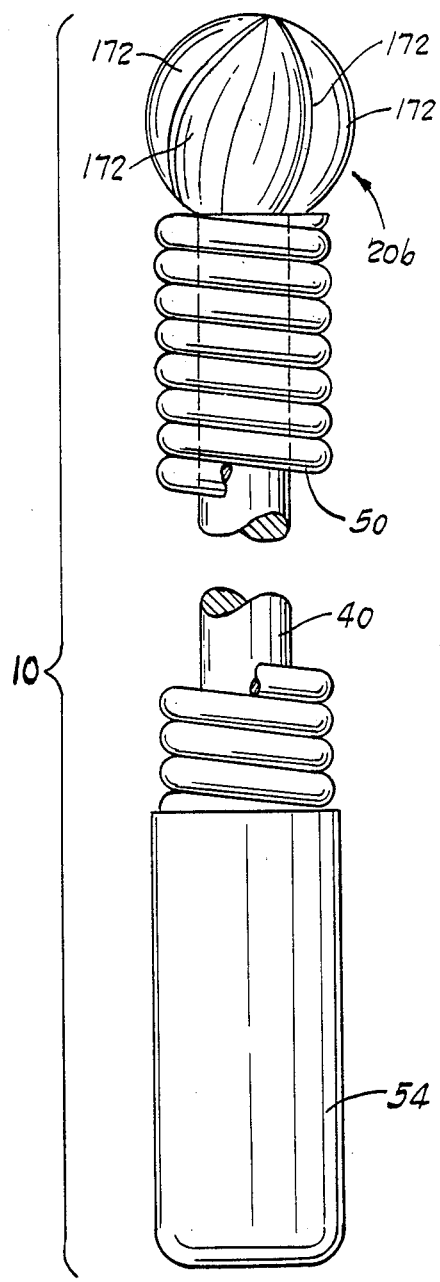
FIG. 10 is a plan view of one distal tip configuration of the FIG. 1 drive catheter.

FIGS. 7-9 depict an alternate drive unit 110 for imparting a reciprocating rotating motion to the distal tip 20b shown in FIG. 10. The drive catheter 10 depicted in FIG. 7 is identical to the drive catheter 10 in FIGS. 2 and 3. To use the drive unit 110 the physician presses the drive bushing 54 (possibly subsequent to manually manipulating the drive catheter 10) into a coupling 120 (FIG. 9) packaged with the drive catheter 10 for attaching the drive catheter 10 to the drive unit 110. The drive unit 110 defines a housing 114 that supports a d.c. motor 132 similar to the motor 80 of FIG. 5. A motor output shaft 134 is coupled to an eccentric drive 136 having a pin 137 coupled to a drive shaft 140. Rotation of the motor output shaft 134 imparts translational back and forth motion to the drive shaft 140. As seen most clearly in FIG. 7, the drive shaft 140 is coupled at one end to a rack drive 150 supported by the drive unit 110. A gear 152 supported by two housing bearings 154 engages the rack 150 to convert translational back and forth motion of the rack drive 150 into reciprocating rotational motion of the gear 152. An output shaft 160 connected to the gear 152 extends through the housing 114. The coupling 120 has an cavity 120a dimensioned to slip over the shaft 160. A threaded connector 170 is then tightened until the connector 170 engages the shaft 160 to prevent relative rotation between the shaft 160 and connector 120.

A motor actuator (not shown) energizes the motor with a battery output and controls the voltage to adjust the rotational output of the motor 132. This controlled rotation of the output shaft 134 results in controlled back and forth movement of the rack 150 which is converted into reciprocating rotation of the output shaft 160 at a preferred rate of approximately 1500 cycles per minute. The amount of reciprocating rotation is controlled by the diameter of the eccentric drive 136.

FIG. 10 illustrates a drive catheter 10 having a specially configured distal tip 20b attached to the distal end of the drive wire 40. The tip 20b is designed for back and forth rotation about a center axis coincident with the drive wire 40. The tip 20b includes a series of equally spaced vanes 172 that form spiral grooves in the tip 20b. Contact between the vanes 172 and the blood vessel obstruction 12 causes abrasion and/or cutting of the obstruction. If desired, suction can be applied to a center passage of the guide catheter 16 to remove material which separates from the vessel 14 during rotation of the tip 20b. This material moves through the guide catheter in a region between the bearing 50 and an inside wall of the guide catheter.

FIGS. 11 and 12 depict a distal tip 20a for use with a drive catheter 10 specifically designed for in and out or ramming motion against the obstructions. A blunt end portion 180 is coupled to enlarged side lobes 182 by lands 184 that widen along the tip length. The lobes 182 are spaced by arcuate grooves or ridges 186 extending along an outer surface of the tip 20a to the vicinity of the blunt end portion 180 of the tip 20a.

In accordance with the invention different diameter drive catheters having different distal tips are chosen for different size blood vessels. A catheter 10 for opening an obstructed coronary artery has a wire bearing 50 of tightly wound (0.006 inch) stainless steel wire coated with teflon to have an outside diameter of 0.025 inch. The center drive wire 40 has an O.D. of 0.010 inch. The tips 20a, 20b are welded to the drive wire 40. Preferably, the tip has a recess or cavity to accommodate the wire 40 and has a width that is about the same as the diameter of the coiled bearing 50. When welded in place the tip 20b (for example) and drive bushing 54 trap the bearing 50 in place about the wire 40 while permitting relative rotation between the tip 20b and bearing 50.

The present invention has been described with a degree of particularity, but it is the intent that the invention include all modifications and alterations from the disclosed design falling within the spirit or scope of the appended claims.

I claim:

1. Apparatus for opening an obstructed region of a patient blood vessel comprising:
   (a) a catheter having
      (i) a distal tip for widening the obstructed region by physically opening a passageway through said obstructed region,
      (ii) an elongated flexible drive shaft coupled to the distal tip and having a length sufficient to extend from a region outside a patient to said obstructed region,
      (iii) a proximal coupling connected to a proximal end portion of the drive shaft for imparting motion to said distal tip via the flexible drive shaft; and (iv) a tightly coiled wire bearing extending a substantial length along the flexible drive shaft between the distal tip and proximal coupling for supporting said drive shaft; and (b) reciprocating means positioned outside the patient and including a motor having an output shaft for imparting a back and forth translational motion to the proximal coupling to impart a reciprocating back and forth translational movement of to the drive shaft within the bearing to translate the distal tip back and forth in a ramming motion against the obstructed region to open the obstructed region of the blood vessel.

2. The apparatus of claim 1 wherein the proximal coupling comprises an enlarged contact member connected to said flexible drive shaft, and a spring for biasing the contact member to one position and said reciprocating means comprises a plunger for contacting the enlarged contact member and moving the contact member against a biasing force of the spring to a second position.

* * * * *